US009801926B2

(12) United States Patent
Lannes et al.

(10) Patent No.: US 9,801,926 B2
(45) Date of Patent: Oct. 31, 2017

(54) METHOD AND COMPOSITION FOR TOPICAL PAIN RELIEF

(71) Applicant: Sweet Relief, Inc., Leesburg, VA (US)

(72) Inventors: Mark A. Lannes, Leesburg, VA (US); Lisa C. Lannes, Leesburg, VA (US); Joe D. Stubblefield, Potomac, MD (US)

(73) Assignee: Sweet Relief, Inc., Leesburg, VA (US)

( * ) Notice: Subject to any disclaimer, the term of this patent is extended or adjusted under 35 U.S.C. 154(b) by 0 days.

(21) Appl. No.: 14/296,759

(22) Filed: Jun. 5, 2014

(65) Prior Publication Data

US 2014/0363420 A1 Dec. 11, 2014

Related U.S. Application Data

(60) Provisional application No. 61/832,323, filed on Jun. 7, 2013, provisional application No. 61/839,024, filed on Jun. 25, 2013.

(51) Int. Cl.
| A61K 38/46 | (2006.01) |
| A61K 38/48 | (2006.01) |
| A61K 31/10 | (2006.01) |
| A61K 36/886 | (2006.01) |
| A61K 36/889 | (2006.01) |

(Continued)

(52) U.S. Cl.
CPC .......... *A61K 38/4873* (2013.01); *A61K 31/10* (2013.01); *A61K 31/723* (2013.01); *A61K 36/22* (2013.01); *A61K 36/28* (2013.01); *A61K 36/30* (2013.01); *A61K 36/534* (2013.01); *A61K 36/61* (2013.01); *A61K 36/736* (2013.01);

(Continued)

(58) Field of Classification Search
None
See application file for complete search history.

(56) References Cited

U.S. PATENT DOCUMENTS

| 7,794,836 | B2 * | 9/2010 | Vasishtha | A23L 1/0029 264/4.1 |
| 2010/0087546 | A1 * | 4/2010 | Appleton | A23L 1/30 514/711 |
| 2012/0156351 | A1 * | 6/2012 | Miyazawa | A23L 1/22083 426/538 |

FOREIGN PATENT DOCUMENTS

WO WO 2011/024471 * 3/2011

OTHER PUBLICATIONS

Robinson, http://www.greenmedinfo.com/blog/36-natural-alternatives-infection1, posted Jul. 6, 2012, accessed Nov. 24, 2015.*
Author Mohammad Najmul Ghani Khan, Title of publication—Khazaain-al-Advia vol. III (20th century AD), Page(s) being submitted—05(p. No. 04-08) ( Ref.pg. No. of publication:477 ), Publication Date—1926 AD, Publisher—Nadeem Yunus Printer / Sheikh Mohd Basheer & Sons, Place of Publication—Lahore.†
Author Mohammad Najmul Ghani Khan, Title of publication—Khazaain-al-Advia vol. I (20th century AD), Page(s) being submitted—05 (p. No. 09-13) ( Ref.pg. No. of publication:666 ), Publication Date—1911 AD, Publisher—Nadeem Yunus Printer / Sheikh Mohd Basheer & Sons, Place of Publication—Lahore.†

(Continued)

*Primary Examiner* — Erin M Bowers

(57) ABSTRACT

A method, product by process, and composition for aiding in pain relief. The user adds hot water to methylsulfonylmethane (MSM), then stirs the resulting mixture until the MSM is dissolved. The user then adds room temperature water, bromelain, aloe vera juice, and papain to the batch, and continues to stir. Coconut oil and palm kernel oil are stirred in, along with a sweet oil mixture. The sweet oil mixture is a mixture of natural, unconcentrated, oils such as lemon oil, sweet orange oil, arnica, sweet almond oil, peppermint oil, grape seed oil, comfrey oil, eucalyptus oil, grapefruit seed extract, and fragrance oils such as mango and kiwi. Finally, xanthan gum is stirred into the mixture, resulting in a batch of desired composition, which can be used topically for pain relief.

12 Claims, 3 Drawing Sheets

(51) Int. Cl.
*A61K 36/752* (2006.01)
*A61K 36/736* (2006.01)
*A61K 36/534* (2006.01)
*A61K 36/87* (2006.01)
*A61K 36/22* (2006.01)
*A61K 36/30* (2006.01)
*A61K 36/61* (2006.01)
*A61K 36/28* (2006.01)
*A61K 31/723* (2006.01)

(52) U.S. Cl.
CPC ............ *A61K 36/752* (2013.01); *A61K 36/87* (2013.01); *A61K 36/886* (2013.01); *A61K 36/889* (2013.01)

(56) References Cited

OTHER PUBLICATIONS

Author—, Title of publication—Caru Cikitsa—Complied by Vaidya Gopinathaji Gupt, Page(s) being submitted—06 (p. No. 14-19) ( Ref.pg. No. of publication:39 ), Publication Date—4th edition 1950, Publisher—Published by Unjha Pharmacy, Place of Publication—Gujarat, India.†

\* cited by examiner
† cited by third party

METHOD AND COMPOSITION FOR TOPICAL PAIN RELIEF

PRIORITY

The present application claims priority to U.S. Provisional Application No. 61/832,323, filed Jun. 7, 2013, and U.S. Provisional Application No. 61/839,024, filed Jun. 25, 2013, the contents of each included herewith in their entirety.

BACKGROUND

1. Technical Field

The present disclosure relates to pain relief and more specifically to a naturally produced topical cream capable of providing pain relief through topical application.

2. Introduction

Many suffering from pain choose to treat the pain with a topical cream or gel. For example, many suffering from sunburn choose to treat the sunburn using aloe applied topically to the burnt skin. Likewise, many who are dealing with muscular aches will apply a topical rubefacient heat rub, such as IcyHot®, to the skin proximal to the sore muscles. However, these products can have various side effects and drawbacks which are undesirable for many users. For instance, some users may desire to treat their aches with natural remedies rather than a combination of chemicals and drugs.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the combinations particularly pointed out in the appended claims. These and other features of the disclosure will become more fully apparent from the following description and appended claims, or can be learned by the practice of the principles set forth herein.

In a first variation, the user adds hot water to methylsulfonylmethane (MSM), then stirs the resulting mixture until the MSM is dissolved. The user then adds room temperature water, bromelain, aloe vera juice, and papain to the batch, and continues to stir. Cocos Nucifera (Coconut) oil and Elaeis Guineensis (Palm Kernel) oil are stirred in, along with a sweet oil mixture. The sweet oil mixture is a mixture of natural, unconcentrated, oils such as: (Citrus Limonum (Lemon) Essential oil, Citrus Sinensis (Sweet Orange) oil, Arnica, Prunus Amygdalus Dulcis (Sweet Almond) Oil, Mentha Piperita (Peppermint) oil, Vitis Vinifera (Grape) Seed Oil, Symphytum Officinale Leaf Extract (Comfrey Oil), Eucalyptus Globulus Essential Oil, Citrus Grandis (Grapefruit) Seed Extract, Fragrance oils—Mango and Kiwi. Finally, xanthan gum is stirred into the mixture, resulting in a batch of desired composition.

In a second variation, the user prepares a mixture of fats, water, and solvents at a lukewarm temperature. The user then adds (while continuing mixing) a warm combination of Bromelain (B), Papain (P), and aloe. The warm combination should be liquid, near the melting point. As the warm combination is added and mixed with the original lukewarm mixture, the temperature of the resulting composite will have a temperature warmer than the lukewarm mixture, but not as warm as the warm combination.

While continuing to mix the resulting composite the user adds natural oils, resulting in an oil blend. The natural oils added are at a cooler temperature, resulting in the temperature of the oil blend being lower again. At this point the user adds an antimicrobial compound, continues mixing, and adds a thickening agent. Finally, the user adds additional oils and water at a lukewarm temperature, continuing to mix until the composition is ready. At this point the composition can be applied topically to sore or injured tissue, resulting in relief.

DETAILED DESCRIPTION

Methods and composition are disclosed which assist in pain relief when the composition is applied topically. Exemplary causes of the pain can be sun burn and neuropathy. The composition is created using natural fruits, nuts, and oils, and can provide aide as (1) a form of aromatherapy, having a tropical scent; (2) a skin moisturizer; and (3) a reducer of swollen/bruised muscles, arthritic pain, neuropathic pain (such as in the hands, feet, or other surface tissues), and sunburn.

Various embodiments of the disclosure are described in detail below. While specific implementations are described, it should be understood that this is done for illustration purposes only. Other components and configurations can be used without parting from the spirit and scope of the disclosure. In addition, while two methods (a preferred method and a second method) are disclosed, method elements and composition elements from either of the disclosed methods can be used, shared, substituted, modified, and/or ignored as needed by a user. For example, should a user suffer allergies for a specific composition element listed below, such element can be removed from the disclosed methods without prejudice. Similarly, combining or deleting steps or stages of the disclosed methods can be performed without prejudice.

Exemplary volumes, weights, etc., provided below are given for purposes of relatedness, i.e., how one volume relates to another volume, not as fixed values. Likewise, the preferred concentrations of all composition elements are naturally occurring concentrations specific to each individual element, and the disclosed volumes/weights presented herein are given with this understanding. While not preferred, diluted or concentrated composition elements can be used. In such instances, the volume and/or weight being used can differ but the mass of the diluted/concentrated composition element should remain within a threshold value of the composition element's mass as disclosed herein.

Figure 1:
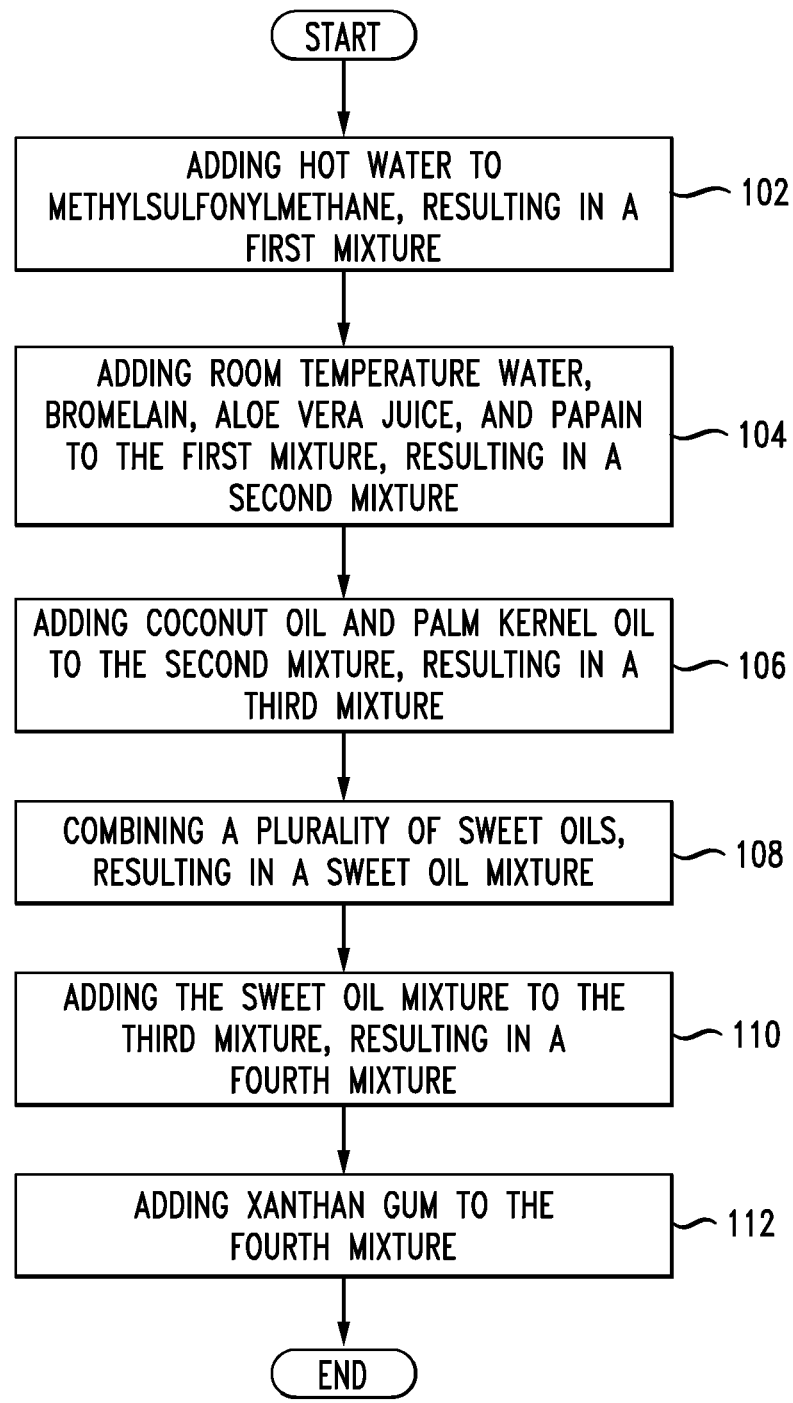
FIG. 1 illustrates a first example method embodiment.

Having provided this introduction, the present disclosure addresses a method and variations of the method for creating a composition which can assist in pain relief. The method will be described from the perspective of a user preparing the composition, although in practice the composition could be prepared using automated machinery. FIG. 1 illustrates a first, preferred, product-by-process description. The product-by-process description uses a series of ingredients which are added in a particular order and mixed under particular conditions.

The ingredients, with amounts in terms of mass or volume, for a preferred exemplary composition of 50 gallons would include:

Methylsulfonylmethane (MSM, $C_2H_6O_2S$)—10.8 kg;
$H_2O$ (Water)—first phase=16 gallons, second phase=2670 mL;
Bromelain (B)—3.69 kg;
Papain—1.44 kg;
Aloe Vera Juice—13 gallons;
Coconut Oil—6 gallons;
Palm Kernel Oil—6 gallons;
Lemon Essential Oil—2457 mL;
Sweet Almond Oil—1323 mL;
Sweet Orange Essential Oil—2268 mL;
Peppermint Oil—756 mL;
Grapeseed Oil—945 mL;
Kiwi Fragrance Oil—819 mL;
Mango Fragrance Oil—1208 mL;
Comfrey Oil—491 mL;
Eucalyptus Oil—491 mL;
Arnica Oil—567 mL;
Grapefruit Seed Extract—126 mL; and
Xanthan Gum—932 g.

To create the 50 gallon composition, the MSM is placed in a large drum capable of holding the finished composition. Ten gallons of hot water (135-150° F.) is then added to the MSM and the combination is stirred at a low stir rate until the MSM is completely dissolved (102), generally approximately 30 seconds. Then the remaining water of the first phase (6 gallons) is added (at room temperature) to the resulting mixture with the bromelain, the aloe vera juice and the papain. That is, the six gallons of room temperature water are mixed into the MSM/hot water mixture at the same time as the bromelain, the aloe vera juice, and the papain (104). All of these elements are stirred together, continuing with the low stir rate, for approximately three minutes.

The coconut oil, palm kernel oil, and second phase of water (the 2670 mL of water at room temperature) are added to the resulting mixture (106), with stirring continuing at a low rate for approximately one minute. The sweet oils (Citrus Limonum (Lemon) Essential oil, Citrus Sinensis (Sweet Orange) oil, Arnica, Prunus Amygdalus Dulcis (Sweet Almond) Oil, Mentha Piperita (Peppermint) oil, Vitis Vinifera (Grape) Seed Oil, Symphytum Officinale Leaf Extract (Comfrey, Oil), Eucalyptus Globulus Essential Oil, Citrus Grandis (Grapefruit) Seed Extract, Fragrance oils, such as Mango and Kiwi, can be previously mixed together. The combined sweet oil mixture goes into the batch (108) all at once after stirring the coconut oil and palm kernel oil. In other configurations, each oil can be added separately to the mixing pot in an iterative fashion, one after the other. In addition, while the ingredient list provided above, while representative of a preferred format, can be modified by adding additional elements, removing elements, and changing the amounts. For example, other configurations can remove various ingredients based on allergies, scent preferences, and/or cost efficiencies. As another example, the specific amounts (volume or mass) of any chemical could be changed to 20% more or less than indicated above. For instance, the ingredients listed above could, if used at all, be used in the following ranges (other amounts and/or ranges could also be used):

Methylsulfonylmethane (MSM, $C_2H_6O_2S$)—8.6-13 kg;
$H_2O$ (Water)—first phase=12.8-19.2 gallons, second phase=2136-3204 mL;
Bromelain (B)—2.952-4.428 kg;
Papain—1.152-1.728 kg;
Aloe Vera Juice—10.4-15.6 gallons;
Coconut Oil—4.8-7.2 gallons;
Palm Kernel Oil—4.8-7.2 gallons;
Lemon Essential Oil—1965.6-2948.4 mL;
Sweet Almond Oil—1058.4-1587.6 mL;
Sweet Orange Essential Oil—1814.4-2721.6 mL;
Peppermint Oil—604.8-907.2 mL;
Grapeseed Oil—756-1134 mL;
Kiwi Fragrance Oil—655.2-982.8 mL;
Mango Fragrance Oil—966.4-1449.6 mL;
Comfrey Oil—392.8-589.2 mL;
Eucalyptus Oil—392.8-589.2 mL;
Arnica Oil—453.6-680.4 mL;
Grapefruit Seed Extract—100.8-151.2 mL; and
Xanthan Gum—745.6-1118.4 g.

At this point the rate of mixing increases from the low rate to a high rate (for example, from 2,000 RPMs to 8,000 RPMs). After approximately two minutes, the sweet oils are distributed throughout the batch, and the xanthan gum is added (110). Upon addition of the xanthan gum the batch begins thickening, and after approximately five minutes of high speed mixing the composition is complete.

Figure 2:
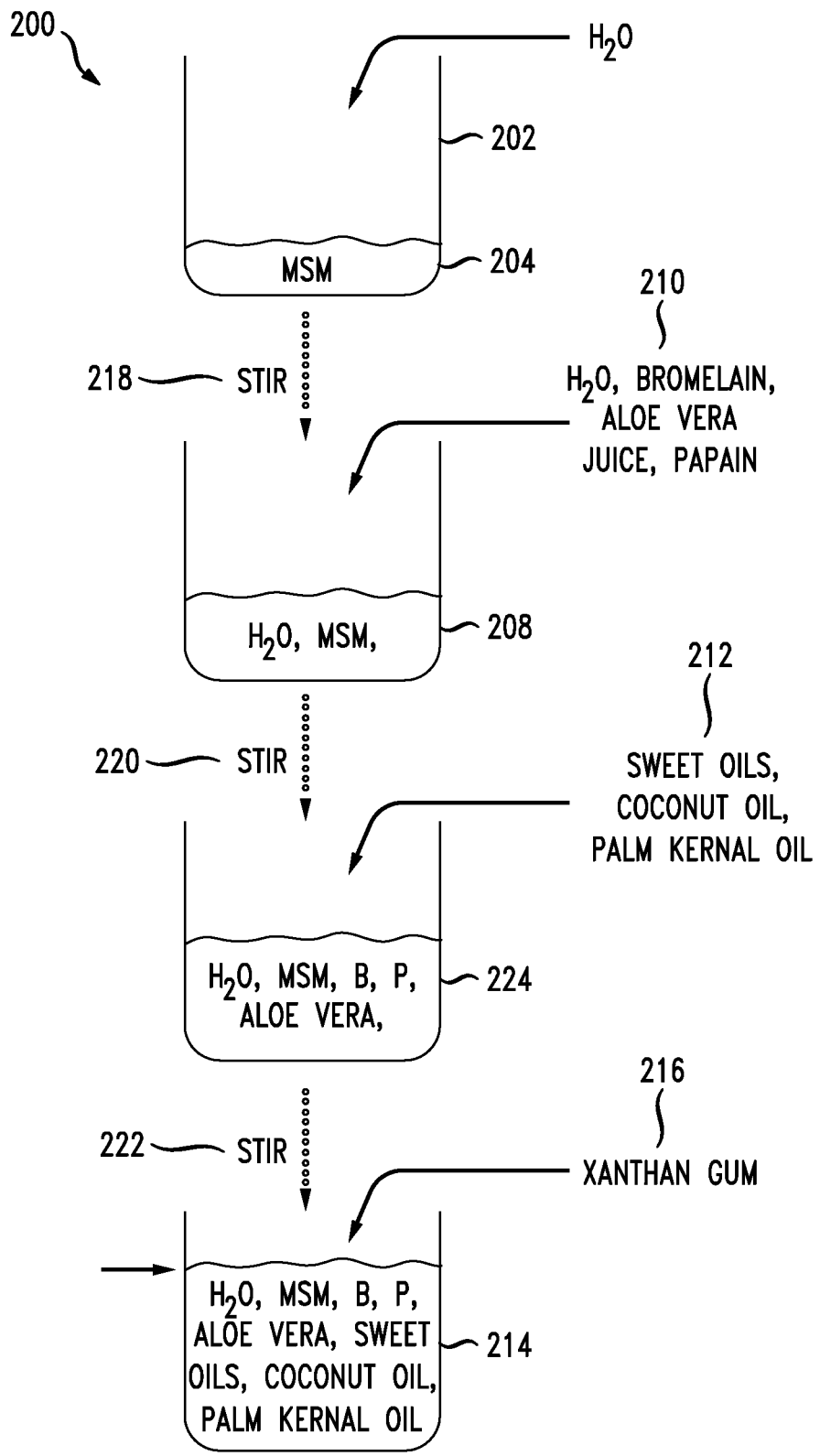
FIG. 2 illustrates an exemplary process to generate a product.
Figure 3:
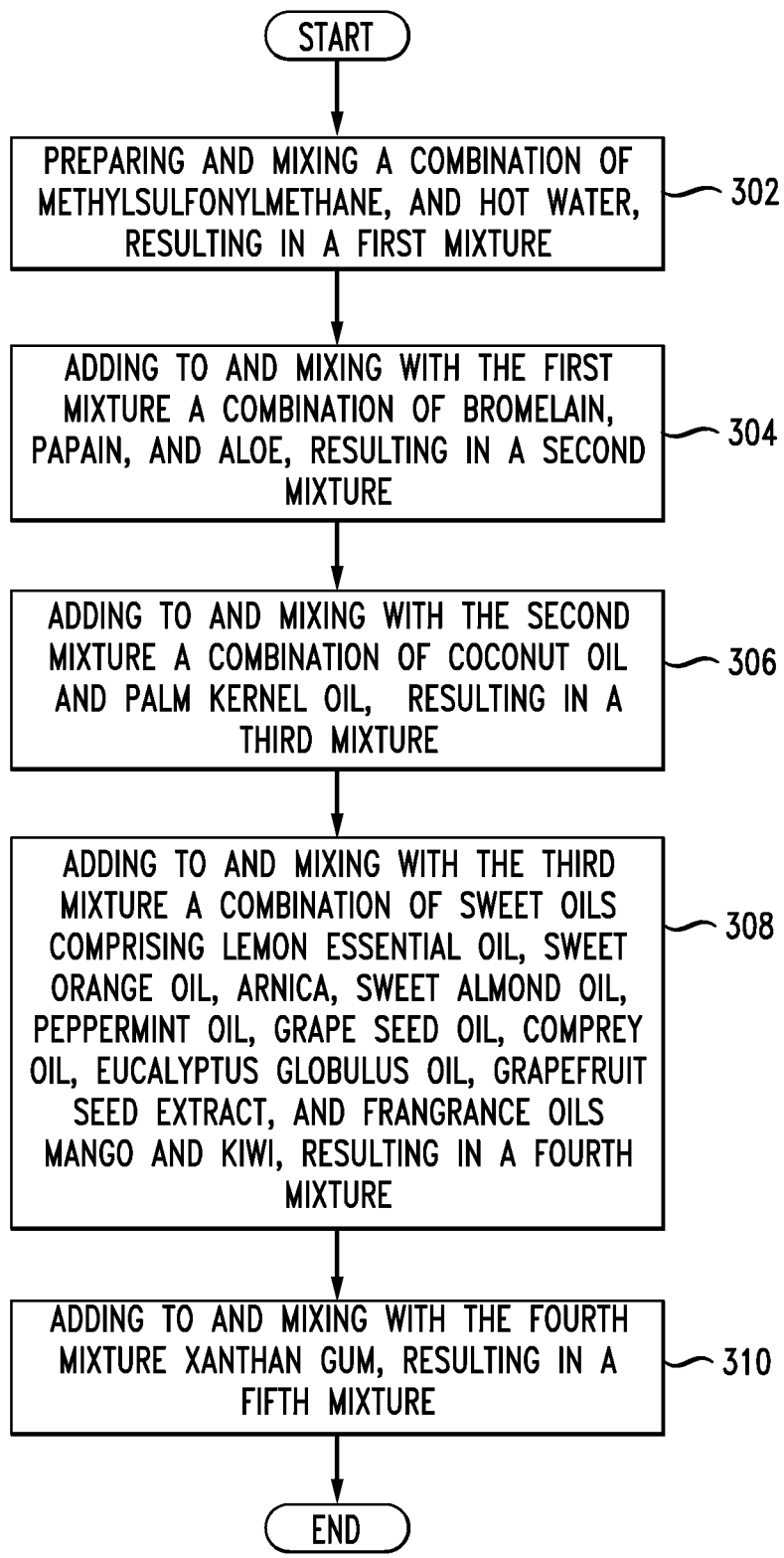
FIG. 3 illustrates a second example method embodiment.

FIG. 2 illustrates an exemplary process 200 to generate the product described in FIG. 1. MSM 204 is placed in a container 202 large enough to accommodate the final product. Water 206 is then added to the MSM 204. The water 206 can be hot (between 135-150° F.), however other temperatures (for example, colder, warmer, or room temperature) can also be used. The combination of the MSM 204 and the water 206 is then stirred 218. The stirring 218 is preferably at a low rate, or RPM (Rotations Per Minute)—for example 1,500-2,000 RPM—but can also be at higher/lower rates, such as 4,000-8,000 RPM. Other configurations can use speeds of stirring which are lower, higher, and/or throttled than the exemplary high rate disclosed.

More water (preferably at room temperature, although other temperatures can be used), bromelain, aloe vera juice, and papain 210 is then added to the combination of MSM and water 208, and the resulting mixture is stirred 220 at the same low rate as previous stirring. In other embodiments, the stirring 220 can be at a different rate than the previous stirring 218. The resulting mixture 224 following the second stirring 220 has a combination of sweet oils, coconut (Cocos Nucifer), palm kernel (Elaeis Guineensis) oil 212 added, and the subsequent stirring 222 switches to a high rate—for example, 12,000 rpm. Other configurations can use speeds of stirring which are lower, higher, and/or throttled than the exemplary high rate disclosed. In addition, users can begin the mixing on a slow speed and ramp up the speed, accelerating throughout the batch process. To the resulting mixture 214 xanthan gum 216 is added. As the combination of the previous mixture 214 and xanthan gum 216 is stirred, the desired product is formed.

In a second version, the user first prepares a mixture of hot water and solvents at a lukewarm temperature (302). The mixture can further include a fat, such as lecithin, and an exemplary solvent is methylsulfonylmethane (MSM, $C_2H_6O_2S$). Exemplary amounts of each component for this portion are 2 cups MSM, and 1700 mL Water. The user mixes these elements together at a rotational rate between 1,500-2,000 rpm, resulting in a first mixture.

The user then prepares a combination of Bromelain, Papain, and Aloe, which is added to the first mixture (304). The warm combination can be added all-together or can be added one element at a time, as well as in any order, so long as the elements are all added prior to the next set of ingredients. For example, if the user wished to add the Papain, then the Aloe, and finally the Bromelain, such an order is acceptable. The temperature of the warm combination should be between 130-150° Fahrenheit. Exemplary amounts of each component are 158 mL Bromelain, 4 tablespoons+1 teaspoon of Papain, and 1950 mL of Aloe. Upon adding all of these warm components to the first mixture, the resulting combination is again mixed between 2,000-3,000 rpm, resulting in a second mixture.

The user then prepares a combination of natural oils (306). These can be added in any order, so long as they are all added prior to the next major ingredient. The combination can be a mixture of coconut (Cocos Nucifer) and palm kernel (Elaeis Guineensis) oils which are heated to between 135-140° F. Additional water can also be added, if needed or desired. Exemplary amounts of the additional coconut oil, palm kernel oil, and water are 50 mL of coconut oil, 50 mL palm kernel oil, and 100 mL water.

To this mixture a blend of sweet oils, which are cooled prior to being added, can be added (308). These sweet oils can include lemon, almond, orange, peppermint, grapeseed, kiwi, mango, comfrey, and eucalyptus oils. More specifically, these "sweet" oils can include combinations of Citrus Limonum (Lemon) Essential oil, Citrus Sinensis (Sweet Orange) oil, Arnica, Prunus Amygdalus Dulcis (Sweet Almond) Oil, Mentha Piperita (Peppermint) oil, Vitis Vinifera (Grape) Seed Oil, Symphytum Officinale Leaf Extract (Comfrey Oil), Eucalyptus Globulus Essential Oil, Citrus Grandis (Grapefruit) Seed Extract, and Fragrance oils such as Mango and Kiwi oils. Various combinations will use one, some, or all of these exemplary oils. In addition, the combination of oils will include arnica. Exemplary amounts of the oils are as follows: 600 mL of (heated) coconut oil, 600 mL of (heated) palm kernel oil, 70 mL of (cooled) lemon oil, 39 mL of (cooled) almond oil, 40 mL of (cooled) orange oil, 20 mL of (cooled) peppermint oil, 25 mL of (cooled) grapeseed oil, 25 mL of (cooled) kiwi oil, 23 mL of (cooled) mango oil, 13 mL of (cooled) comfrey oil, and 13 mL of (cooled) eucalyptus oil. The arnica can have a volume of 0.5-1 cups, and can also be cooled. Once the various oils have been added to the second mixture, the elements are mixed together, resulting in a third mixture.

The specific oils used can be added to or removed. For instance, in certain combinations mango oil might be removed. Alternatively, the volumes of specific oils used can vary. An exemplary range of oil volumes can read:

Coconut Oil—480-720 ml;
Palm Kernel Oil—480-720 ml;
Lemon Oil—56-84 ml;
Almond Oil—44.8-67.2 ml;
Orange Oil—32-48 ml;
Peppermint Oil—16-24 ml;
Grapeseed Oil—20-30 ml;
Kiwi Oil—20-30 ml;
Comfrey Oil—10.4-15.6 ml; and
Eucalyptus Oil—10.4-15.6 ml.

To the third mixture the user can, if desired, add citricidal extract or a different antimicrobial compound. This is a very small amount in comparison with other elements previously added—generally on the order of 3-4 mL. After adding the citricidal extract the user continues mixing, resulting in a fourth mixture.

The user adds a thickening agent, such as Xanthan gum to the fourth mixture (310). An exemplary volume of the Xanthan gum is 55 mL. After adding the thickening agent to the fourth mixture, the user again mixes, resulting a fifth mixture.

With these additional oils and water added to mixture the fifth mixture, the user continues mixing, and the composition is ready to be applied to sore or achy tissues.

As disclosed above, all mixing in the second embodiment is performed between 2,000 and 12,000 rpm. In addition, once the natural oils are added to the second mixture, it is desirable to maintain the temperature of the composition at or below room temperature. The temperatures of the natural oils can be chilled to accommodate this desire.

The various embodiments described above are provided by way of illustration only and should not be construed to limit the scope of the disclosure. For example, the principles herein can be used in a variety of combinations, using various natural oils, fats, and other natural ingredients. Exact amounts of the various composition elements/ingredients can be modified, replaced, or even removed, without going against the disclosed invention. In addition, components of the various embodiments described herein can be used by other configurations without prejudice or disclaimer, such as the amounts of the composition elements being used in the first embodiment also being used in the second disclosed embodiment and vice versa. Various modifications and changes may be made to the principles described herein without following the example embodiments and applications illustrated and described herein, and without departing from the spirit and scope of the disclosure.

We claim:

1. A method of preparing a composition of topical cream for topical pain relief, the method comprising:
   adding first water to methylsulfonylmethane, resulting in a first mixture;
   adding second water, bromelain, aloe vera juice, and papain to the first mixture, resulting in a second mixture;
   heating coconut oil and palm kernel oil;
   adding the coconut oil and the palm kernel oil to the second mixture, resulting in a third mixture;
   combining a plurality of sweet oils, resulting in a sweet oil mixture, wherein the plurality of sweet oils comprises more than one of: lemon oil, sweet orange oil, arnica, sweet almond oil, peppermint oil, grape seed oil, comfrey oil, eucalyptus oil, grapefruit seed extract, and fragrance oils comprising mango oil and kiwi oil;
   adding the sweet oil mixture, at a temperature lower than the third mixture, to the third mixture, resulting in a fourth mixture; and
   thickening the fourth mixture comprising adding xanthan gum to the fourth mixture, resulting in the composition, wherein each element, when added, has one of a volume and a mass
in a range comprising:
   the methyl sulfonylmethane: 8.6-13 kg;
   the first water: 12.8-19.2 gallons;
   the second water: 2136-3204 mL;
   the bromelain: 2.952-4.428 kg;
   the papain: 1.152-1.728 kg;
   the aloe vera juice: 10.4-15.6 gallons;
   the coconut oil: 4.8-7.2 gallons;
   the palm kernel oil: 4.8-7.2 gallons;
   the lemon essential oil: 1965.6-2948.4 mL;
   the sweet almond oil: 1050.4-1587.6 mL;
   the sweet orange essential oil: 1814.4-2721.6 mL;
   the peppermint oil: 604.8-907.2 mL;
   the grapeseed oil: 756-1134 mL;
   the kiwi fragrance oil: 655.2-982.8 mL;
   the mango fragrance oil: 966.4-1449.6 mL;
   the comfrey oil: 392.8-589.2 mL;

the eucalyptus oil: 392.8-589.2 mL;
the arnica oil: 453.6-680.4 mL;
the grapefruit seed extract: 100.8-151.2 mL; and
the xanthan gum: 745.6-1118.4
wherein the composition is a topical cream suitable for application to skin and provides topical pain relief when applied to the skin.

2. The method of claim 1, wherein the first water is at a temperature between 135-150° F., inclusive.

3. The method of claim 2, wherein the second water is at a room temperature.

4. The method of claim 1, further comprising:
stirring the first mixture and the second mixture at a lower rate; and
stirring the third mixture, the fourth mixture, and the composition at a higher rate, wherein the lower rate and higher rate are with respect to one another.

5. The method of claim 4, wherein the lower rate is 1,500 rpm and the higher rate is 12,000 rpm.

6. The method of claim 1, further comprising adding an antimicrobial compound to the fourth mixture.

7. A composition of topical cream for topical pain relief prepared by:
adding first water to methylsulfonylmethane, resulting in a first mixture;
adding second water, bromelain, aloe vera juice, and papain to the first mixture, resulting in a second mixture;
heating coconut oil and palm kernel oil;
adding the heated coconut oil and the heated palm kernel oil to the second mixture, resulting in a third mixture;
combining a plurality of sweet oils, at a temperature lower than the third mixture, resulting in a sweet oil mixture, wherein the plurality of sweet oils comprises more than one of: lemon oil, sweet orange oil, arnica, sweet almond oil, peppermint oil, grape seed oil, comfrey oil, eucalyptus oil, grapefruit seed extract, and fragrance oils comprising mango oil and kiwi oil;
adding the sweet oil mixture to the third mixture, resulting in a fourth mixture; and
thickening the fourth mixture comprising adding xanthan gum to the fourth mixture, resulting in the composition,
wherein each element, when added, has one of a volume and a mass in a range comprising:
the methyl sulfonylmethane: 8.6-13 kg;
the first water: 12.8-19.2 gallons;
the second water: 2136-3204 mL;
the bromelain: 2.952-4.428 kg;
the papain: 1.152-1.728 kg;
the aloe vera juice: 10.4-15.6 gallons;
the coconut oil: 4.8-7.2 gallons;
the palm kernel oil: 4.8-7.2 gallons;
the lemon essential oil: 1965.6-2948.4 mL;
the sweet almond oil: 1050.4-1587.6 mL;
the sweet orange essential oil: 1814.4-2721.6 mL;
the peppermint oil: 604.8-907.2 mL;
the grapeseed oil: 756-1134 mL;
the kiwi fragrance oil: 655.2-982.8 mL;
the mango fragrance oil: 966.4-1449.6 mL;
the comfrey oil: 392.8-589.2 mL;
the eucalyptus oil: 392.8-589.2 mL;
the arnica oil: 453.6-680.4 mL;
the grapefruit seed extract: 100.8-151.2 mL; and
the xanthan gum: 745.6-1118.4 g,
wherein the composition is a topical cream suitable for application to skin and provides topical pain relief when applied to the skin.

8. The composition of claim 7, wherein the first water is at a temperature between 135-150° F., inclusive.

9. The composition of claim 8, wherein the second water is at a room temperature.

10. The composition of claim 7, wherein the composition is further prepared by:
stirring the first mixture and the second mixture at a lower rate; and
stirring the third mixture, the fourth mixture, and the composition at a higher rate, wherein the lower rate and higher rate are with respect to one another.

11. The composition of claim 10, wherein the lower rate is 2,000 rpm and the higher rate is 12,000 rpm.

12. The composition of claim 7, wherein the composition is further prepared by adding an antimicrobial compound to the fourth mixture.

* * * * *